United States Patent
Gibson (10) Patent No.: US 8,133,215 B2
(45) Date of Patent: Mar. 13, 2012

(54) INDEPENDENTLY-MANUFACTURED DRUG DELIVERY MODULE AND CORRESPONDING RECEPTACLE IN AN IMPLANTABLE MEDICAL DEVICE

(75) Inventor: Peter Gibson, South Coogee (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 12/191,302

(22) Filed: Aug. 13, 2008

(65) Prior Publication Data
US 2009/0048580 A1   Feb. 19, 2009

Related U.S. Application Data

(60) Provisional application No. 60/955,530, filed on Aug. 13, 2007.

(51) Int. Cl.
*A61K 9/22* (2006.01)
*A61M 37/00* (2006.01)
(52) U.S. Cl. ............... 604/891.1; 604/288.01
(58) Field of Classification Search .......... 604/11, 604/285–287, 514, 890.1, 891.1, 288.01; 424/437; 514/956
See application file for complete search history.

(56) References Cited

U.S. PATENT DOCUMENTS

| | | |
|---|---|---|
| 3,890,977 A | 6/1975 | Wilson |
| 4,046,151 A | 9/1977 | Rose |
| 4,154,247 A | 5/1979 | O'Neill |
| 4,306,563 A | 12/1981 | Iwatschenko |
| 4,351,337 A | 9/1982 | Sidman |
| 4,357,497 A | 11/1982 | Hohmair et al. |
| 4,381,013 A | 4/1983 | Dutcher |
| 4,506,680 A | 3/1985 | Stokes |
| 4,532,930 A | 8/1985 | Crosby et al. |
| 4,762,135 A | 8/1988 | van der Puije et al. |

(Continued)

FOREIGN PATENT DOCUMENTS

DE   10032000   1/2001

(Continued)

OTHER PUBLICATIONS

International Search Report for PCT/AU01/01232, dated Oct. 26, 2001.

(Continued)

*Primary Examiner* — Kevin C Sirmons
*Assistant Examiner* — Bradley Osinski
(74) *Attorney, Agent, or Firm* — Kilpatrick, Townsend & Stockton, LLP (57) ABSTRACT

A drug delivery system for an implantable medical device and methods for making and using the same. Embodiments include a housing of an implantable component of the medical device and one or more at least quasi-solid drug-delivery modules that retain an at least quasi-solid state if not a solid state. The drug-delivery modules and component housing are physically distinct, and as such, may be manufactured independently of each other. The independently-manufacturable drug delivery modules each carry a drug, while the component housing has an exterior surface with one or more recesses formed therein. Associated module(s) and recess(es) are correspondingly dimensioned so that each module may be securely retained within an associated recess via, for example, an interference fit such as by physical interlocking or by friction fit. When so retained in a housing recess, the drug-delivery module and surrounding exterior surface of the housing form a contiguous component surface.

24 Claims, 5 Drawing Sheets

U.S. PATENT DOCUMENTS

| | | | |
|---|---|---|---|
| 4,784,161 | A | 11/1988 | Skalsky et al. |
| 4,819,662 | A | 4/1989 | Heil, Jr. et al. |
| 4,844,099 | A | 7/1989 | Skalsky et al. |
| 4,972,848 | A | 11/1990 | Di Domenico et al. |
| 4,994,069 | A | 2/1991 | Ritchart et al. |
| 5,066,278 | A | 11/1991 | Hirschberg et al. |
| 5,092,332 | A | 3/1992 | Lee et al. |
| 5,265,608 | A | 11/1993 | Lee et al. |
| 5,458,631 | A | 10/1995 | Xavier |
| 5,474,542 | A | 12/1995 | Ghandi et al. |
| 5,531,780 | A | 7/1996 | Vachon |
| 5,554,114 | A | 9/1996 | Wallace et al. |
| 5,645,585 | A | 7/1997 | Kuzma |
| 5,653,742 | A | 8/1997 | Parker et al. |
| 5,697,951 | A | 12/1997 | Harpstead et al. |
| 5,755,474 | A | 5/1998 | Slomski |
| 5,755,765 | A | 5/1998 | Hyde et al. |
| 5,769,077 | A | 6/1998 | Lindegren et al. |
| 5,782,744 | A | 7/1998 | Money et al. |
| 5,902,329 | A | 5/1999 | Hoffmann et al. |
| 5,929,041 | A | 7/1999 | Magal |
| 5,975,085 | A | 11/1999 | Rise |
| 6,038,482 | A | 3/2000 | Vachon |
| 6,038,484 | A | 3/2000 | Kuzma |
| 6,078,841 | A | 6/2000 | Kuzma |
| 6,119,044 | A | 9/2000 | Kuzma |
| 6,125,302 | A | 9/2000 | Kuzma |
| 6,163,729 | A | 12/2000 | Kuzma |
| 6,259,951 | B1 | 7/2001 | Kuzma et al. |
| 6,304,787 | B1 | 10/2001 | Kuzma et al. |
| 6,309,410 | B1 | 10/2001 | Kuzma et al. |
| 6,398,758 | B1 | 6/2002 | Jacobson et al. |
| 6,421,569 | B1 | 7/2002 | Treaba et al. |
| 7,206,639 | B2 | 4/2007 | Jacobsen et al. |
| 7,272,449 | B2 | 9/2007 | Dadd et al. |
| 7,571,012 | B2 | 8/2009 | Gibson |
| 2002/0032477 | A1 | 3/2002 | Helmus et al. |
| 2002/0077685 | A1 | 6/2002 | Sundquist et al. |
| 2003/0045921 | A1 | 3/2003 | Dadd et al. |
| 2003/0097121 | A1 | 5/2003 | Jolly et al. |
| 2003/0181967 | A1 | 9/2003 | Dadd et al. |
| 2004/0030376 | A1 | 2/2004 | Gibson et al. |
| 2004/0078057 | A1 | 4/2004 | Gibson |
| 2004/0116995 | A1 | 6/2004 | Dadd |
| 2004/0122501 | A1 | 6/2004 | Dadd et al. |
| 2005/0177118 | A1* | 8/2005 | Hoganson et al. ........ 604/288.01 |
| 2005/0256560 | A1* | 11/2005 | Lenarz et al. ................. 607/137 |
| 2006/0287689 | A1 | 12/2006 | Debruyne et al. |
| 2007/0184085 | A1* | 8/2007 | Radhakrishnan et al. .... 424/423 |
| 2008/0033520 | A1 | 2/2008 | Jolly |
| 2009/0062896 | A1 | 3/2009 | Overstreet et al. |
| 2009/0292237 | A1 | 11/2009 | Overstreet et al. |

FOREIGN PATENT DOCUMENTS

| | | |
|---|---|---|
| EP | 0002 068 | 5/1979 |
| EP | 0007157 | 1/1980 |
| EP | 0350 188 A1 | 1/1990 |
| EP | 0 602 859 A2 | 6/1994 |
| EP | 0653223 | 5/1995 |
| EP | 0706807 | 4/1996 |
| EP | 0 739 642 A2 | 10/1996 |
| EP | 0773037 | 5/1997 |
| EP | 0 778 043 A1 | 6/1997 |
| EP | 0 778 044 A2 | 6/1997 |
| EP | 0 778 044 A3 | 6/1997 |
| EP | 0 783 900 A2 | 7/1997 |
| EP | 0 783 901 A2 | 7/1997 |
| EP | 0 784 994 A1 | 7/1997 |
| EP | 0784 995 A1 | 7/1997 |
| EP | 0 919 254 A2 | 6/1999 |
| GB | 2 217 993 A | 11/1989 |
| JP | 55-190 | 5/1980 |
| JP | 8-229 137 | 9/1996 |
| JP | 9-508054 | 9/1997 |
| JP | 11-514252 | 11/1999 |
| WO | WO 96/15665 | 5/1996 |
| WO | 9710784 | 3/1997 |
| WO | WO 97/10784 | 3/1997 |
| WO | WO 99/00067 | 1/1999 |
| WO | WO 99/11321 | 3/1999 |
| WO | WO 99/55360 | 11/1999 |
| WO | WO 00/56399 | 9/2000 |
| WO | WO 00/57949 | 10/2000 |
| WO | WO 00/71063 | 11/2000 |
| WO | WO 01/41674 | 6/2001 |
| WO | WO 02/32498 | 4/2002 |
| WO | 0241666 | 5/2002 |
| WO | WO 02/41666 | 5/2002 |
| WO | WO 02/055136 | 7/2002 |
| WO | WO 02055136 | 7/2002 |
| WO | WO 02/082234 | 10/2002 |
| WO | WO 03/049658 | 6/2003 |
| WO | WO 03/072193 | 9/2003 |
| WO | WO 03072193 | 9/2003 |
| WO | WO 2009/124041 | 10/2009 |
| WO | WO 2010/045432 | 4/2010 |

OTHER PUBLICATIONS

International Preliminary Examination Report for PCT/AU01/01232 dated Feb. 25, 2002.

Australian Patent Office International-Type-Search Report, PR 0541 dated Dec. 20, 2000.

Australian Patent Office International-Type-Search Report, PR 0542, dated Dec. 20, 2000.

International Search Report for PCT/AU01/01231, dated Oct. 26, 2001.

European Supplemental Search Report, dated Jan. 22, 2004; corresponding Application No. 01973835.0-2305; Applicant Cochlear Limited.

Research Disclosure; Nov. 1997; No. 403-40349, 790-791pp; "Epicardial-Transvenous Left Ventricular Lead with Dual Ring Electrodes (Cathode Ring & Anode Ring) Design"; by Disclosed Anonymously, K. Mason Publications, Ltd., England.

Research Disclosure; Nov. 1997; No. 403-40342, 785pp; "Epicardial-Transvenous Left Atrial Lead with Wound 'Butterfly Tongue' Electrode"; by Disclosed Anonymously, K. Mason Publications, Ltd., England.

Australian International-Type Search Report dated Dec. 15, 2000; priority National Application PR 0684; Applicant Cochlear Limited.

Australian International-Type Search Report dated Dec. 15, 2000; priority National Application PR 0807; Applicant Cochlear Limited.

Australian International-Type Search Report dated Dec. 15, 2000; priority National Application PR 1005; Applicant Cochlear Limited.

PCT International Search Report: PCT/AU01/01230;—filed Sep. 28, 2001;—Applicant: Cochlear Limited.

PCT International Preliminary Examination Report: PCT/AU01/01230;—filed Sep. 28, 2001;—Applicant: Cochlear Limited.

Notice of Reason(s) for Rejection, related to Japanese Patent Application No. P2002-543261, Jan. 9, 2007.

Australian Examination Report related to Patent Application No. 2002223270. Dated Aug. 17, 2006.

Canadian Examination Report related to Patent Application No. 2,428,542, May 15, 2009.

European Examination Report dated Apr. 20, 2007, related to Application No. 01994538.5; Applicant Cochlear Limited.

International Search Report dated Nov. 29, 2001; corresponding PCT/AU01/01479, filed Dec. 2, 2001 published as WO 2002/4166 on May 23, 2002; Applicant Cochlear Limited; Inventor: Peter Gibson.

Written Opinion dated 01.28.20021; corresponding PCT/AU01/01479, filed Dec. 2, 2001 published as WO 2002/4166 on May 23, 2002; Applicant Cochlear Limited; Inventor: Peter Gibson.

International Preliminary Examination Report dated Oct. 4, 2002; corresponding PCT/AU01/01479, filed Dec. 2, 2001 published as WO 2002/4166 on May 23, 2002; Applicant Cochlear Limited; Inventor: Peter Gibson.

Altschulere, et al., Rescue and Regrowth of Sendory Nerves Following Deafferentation by Neurotrophic factors, Annals New York Academy of Sciences.

Supplemental European Search Report. EP 01994538. Mailed May 27, 2005.

European Patent Office Extended Search Report for EP 08253298, dated Dec. 30, 2008.
Final Office Action for U.S. Appl. No. 12/535,374 mailed Jun. 21, 2010.
Non-Final Office Action for U.S. Appl. No. 10/416,634, mailed May 9, 2008.
Non-Final Office Action for U.S. Appl. No. 10/416,634, mailed Feb. 28, 2007.
Non-Final Office Action for U.S. Appl. No. 10/416,634, mailed Oct. 4, 2006.
EP Office Communication for EP Application No. 08253298.7, dated Jul. 14, 2010.
Extended European Search Report for EP Application No. 08523298.7, dated Jan. 14, 2009.
EP Official Communication pursuant to Article 94(3) EPC in EP Application No. 08253298.7, dated Nov. 6, 2009.
Response to EP Office Action EP Application No. 08253298.7, filed Mar. 16, 2010.
Non-final Office Action for U.S. Appl. No. 10/416,634, mailed Apr. 6, 2006.
Non-Final Office Action for U.S. Appl. No. 10/416,634, mailed Oct. 1, 2007.

* cited by examiner

INDEPENDENTLY-MANUFACTURED DRUG DELIVERY MODULE AND CORRESPONDING RECEPTACLE IN AN IMPLANTABLE MEDICAL DEVICE

CROSS-REFERENCE TO RELATED APPLICATIONS

This application claims the benefit of U.S. Provisional Application No. 60/955,530, entitled "An Independently-Manufactured Drug Delivery Module And Corresponding Receptacle In An Implantable Medical Device," filed Aug. 13, 2007 under Attorney Docket No. 22409-00147-US, which is hereby incorporated by reference herein.

BACKGROUND

1. Field of the Invention

The present invention relates generally to implantable medical devices, and more particularly, to an independently-manufactured drug delivery module and corresponding recess in an implantable medical device.

2. Related Art

Medical devices having one or more implantable components, generally referred to as implantable medical devices, have provided a wide range of therapeutic benefits to patients over recent decades. One type of implantable medical device that has provided substantial benefits to patients over the years is a prosthetic hearing device. Prosthetic hearing devices process ambient sound to supplement or provide hearing ability to a hearing impaired patient.

Prosthetic hearing devices include a category of implantable devices known as Cochlear™ implants (also referred to as Cochlear™ devices, Cochlear™ implant devices, and the like; "cochlear implants" herein). (COCHLEAR is a trademark of Cochlear Limited, Lane Cove, NSW, Australia.). Cochlear implants include an array of stimulation electrodes which is implanted in the cochlea of the patient (referred to herein as a recipient). The electrode carrier member is controlled by an electronic system encased in a hermetically sealed, biocompatible housing typically implanted in the mastoid. The electronic system, commonly referred to as a stimulator unit, essentially contains decoder and driver circuits for the stimulation electrodes. Acoustic sound reception and conversion of acoustic signals into electrical signals typically occurs externally in a speech processor worn by the recipient. The speech processor superimposes the preprocessed signals, properly coded, on a high frequency carrier signal which is transmitted transcutaneously to the implanted components through the closed skin. A microphone is located outside of the recipient's body, typically in a behind-the-ear housing worn on the auricle.

Traditionally, there has been interest in delivering a bioactive substance or chemical (collectively "drug" herein) in conjunction with implantable medical devices. For example, in one conventional approach the implantable medical device is coated with a drug. In other conventional approaches, a drug is integrated into the polymeric coating of the implantable medical device component. These and other conventional approaches typically require the incorporation of the drug into the material of the implantable medical device during the manufacturing process of the device. This introduces a number of difficult problems and challenges for the manufacturing and sterilization of medical devices, particularly complex medical devices.

In other conventional approaches, drugs in liquid form are delivered to an implanted component and/or its surrounding tissue via an external or implanted reservoir. However, the use of reservoirs provides significant limitations to many aspects of the administration of the drug therapy.

SUMMARY

In accordance with one aspect of the present invention, a drug-delivery system for an implantable medical device is disclosed, the device comprising: a housing of an implantable component of the medical device having an exterior surface with one or more recesses formed therein; a drug-delivery module that retains at least a quasi-solid state and releasably carries at least one drug; wherein the module and housing are physically distinct, and the module and recess are correspondingly dimensioned such that the module may be securely retained within the recess.

In accordance with another aspect of the present invention, a method for implanting a drug delivery system in connection with an implantable medical device is disclosed, the method comprising: producing a drug-delivery module that releasably carries at least one drug; producing, independently of the drug-delivery module, a housing for the implantable medical device component, the housing having an exterior surface with at least one recess formed therein, wherein the module(s) and recess(es) are correspondingly configured so that the module(s) may be securely retained within a corresponding recess; and inserting the drug-delivery module into the recess subsequent to the device's manufacture.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a drug delivery system for an implantable medical device and methods for making and using the same. Embodiments of the drug delivery system comprise a housing of an implantable component of the medical device and one or more at least quasi-solid drug-delivery modules that retain an at least quasi-solid state if not a solid state. The drug-delivery modules and component housing are physically distinct, and as such, may be manufactured independently of each other. The independently-manufacturable drug delivery modules each carry a drug, while the component housing has an exterior surface with one or more recesses formed therein. Associated module(s) and recess(es) are correspondingly dimensioned so that each module may be securely retained within an associated recess via, for example, an interference fit such as by physical interlocking or by friction fit. When so retained in a housing recess, the drug-delivery module and surrounding exterior surface of the housing form a contiguous component surface.

Providing a quasi-solid or solid drug delivery module and implantable medical device component housing increases flexibility in the applied therapy while reducing the undesirable aspects associated with conventional uses of drugs in connection with implantable medical devices. For example, because it may be manufactured independently of the component housing, the drug delivery module may be integrated into the implantable component housing; that is, inserted into an associated recess, subsequent to the device's manufacture and/or sterilization, and prior to, concurrently with, or subsequent to the implantation of the medical device component. As another example, the present invention may enable manufacturing efforts to be focused solely on the successful manufacture of the medical device. This may result in reduced manufacturing costs, reduced drug yield loss, reduced handling and contamination of drugs, and other advantages over conventional techniques. Furthermore, the implantable medical device component and the drug delivery modules to be made by different manufacturers. Specifically, an implantable medical device manufacturer may outsource the manufacture of the drug deliver modules to a third party manufacturer that specializes in making such products. Such outsourcing may provide further benefits such as the reduction of the cost of research and development by outsourcing to manufacturers that already have regulatory approval for the desired drugs. This in turn may facilitate the commercialization of a medical device incorporating the drug delivery modules. Additionally, certain embodiments of the implantable medical device may be utilized as a universal device having a standardized recess which may be loaded with different embodiments of drug delivery modules. This advantageously enables a single implantable medical device component to be manufactured and inventoried without consideration of the availability of a particular drug, the shelf life of the drug-delivery modules, the dosage requirements of the recipient, and so on.

As used herein, the term "drug" refers to any bioactive substance or chemical now or later developed, including, but not limited to, pharmaceuticals and other chemical compounds such as those intended to provide therapeutic benefits to, or other acute or chronic reactions in, an implant recipient, whether localized or systemic. Such drugs may include, for example, steroids or other anti-inflammatory drugs to reduce inflammation at the implantation site. Other drugs that may be included in the drug delivery modules are antibiotics to mitigate bacterial growth related to the implantation of the medical device. Other drugs may be utilized to increase the performance of the implantable medical device.

Figure 1:
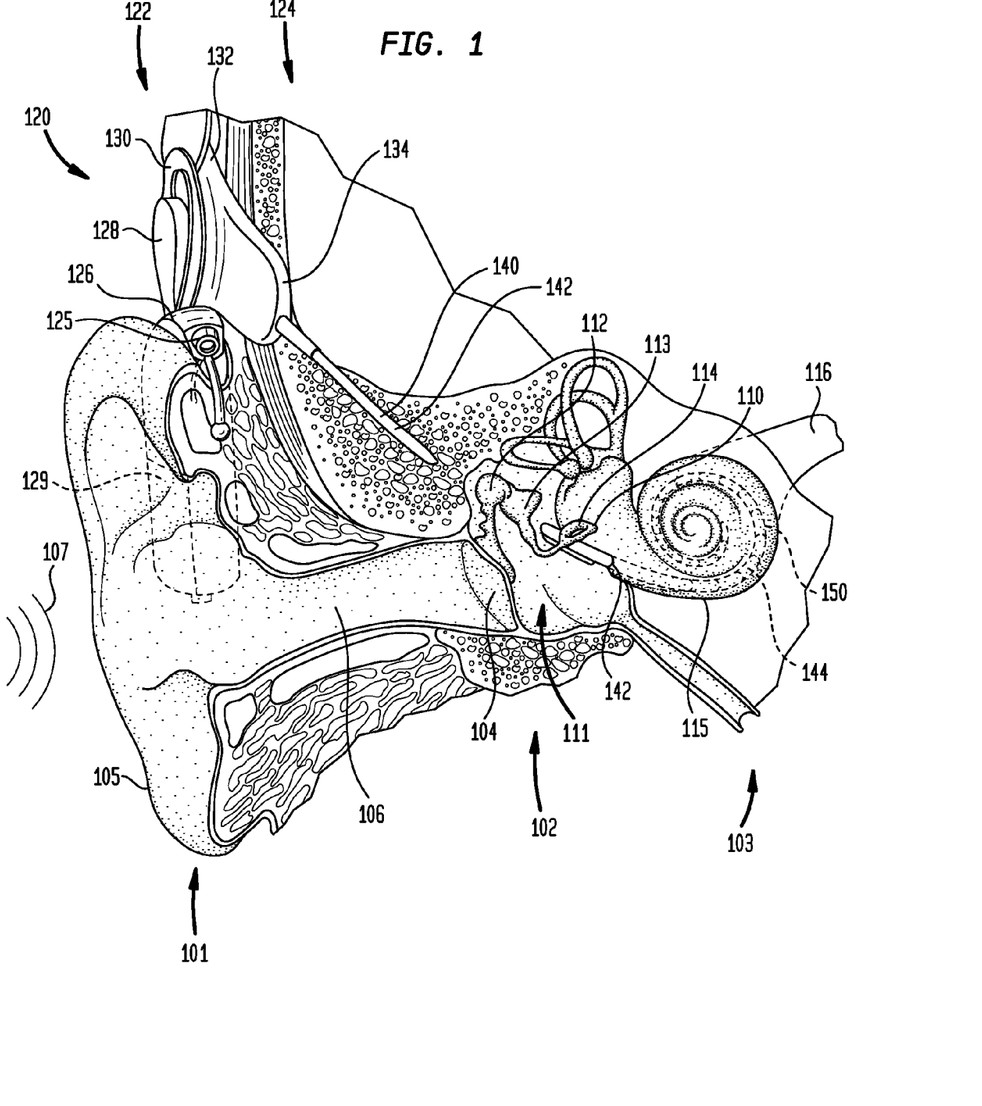
FIG. 1 is a perspective view of an exemplary implantable medical device, a cochlear implant, in which embodiments of the drug delivery system of the present invention may be advantageously implemented.

FIG. 1 is a perspective view of an exemplary implantable medical device in which embodiments of a drug delivery system of the present invention may be implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants such a cochlear implant 120 is utilized to directly stimulate the ganglion cells to provide a hearing sensation to the recipient.

FIG. 1 also shows the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Internal component assembly 124 comprise an internal coil 132 of a stimulator unit 134 that receives and transmits power and coded signals received from external assembly 122 to other elements of stimulator unit 134 which apply the coded signal to cochlea 115 via an implanted electrode assembly 140. Electrode assembly 140 enters cochlea 115 at cochleostomy region 142 and has one or more electrodes 150 positioned on an electrode array 144 to be substantially aligned with portions of tonotopically-mapped cochlea 115. Signals generated by stimulator unit 134 are typically applied by an array 144 of electrodes 150 to cochlea 115, thereby stimulating auditory nerve 116.

Given the coiled shape of cochlea 115, electrode carrier member 142 is typically constructed using a material, or combination of materials, which curls or is capable of being curled in a manner which follows the curvature of cochlea 115. The portion of electrode assembly 140 intended to be inserted into cochlea 115 will often have a stiffening stylet (not shown) inserted into a channel, for example a lumen (not shown), which extends distally from the proximate end of electrode carrier member 142. During implantation of electrode assembly 140, the stylet contained in the lumen of carrier member 142 is removed from the proximate end of the carrier member as the carrier member is inserted into cochlea 115. The act of removing the stiffening stylet from the lumen allows electrode carrier member 142 to curl. In further embodiments of cochlear implant 120, the stiffness of the stylet decreases in response to fluids and/or body temperature allowing electrode carrier member 142 to curl in order to follow the curvature of the inner walls of cochlea 115. In other embodiments of cochlear devices, electrode carrier member 142 is naturally straight without the assistance of a stylet inserted into the lumen. Such embodiments of electrode carrier member 142 are constructed using a flexible material, or is constructed so as to flex upon a fixed amount of force being exerted on the tip or body of electrode carrier member 142 as it is being inserted into cochlea 115. If further embodiments of implanted cochlear devices, a stylet may be inserted into the lumen of electrode carrier member 142, where the stylet interact with fluids and/or some level of body temperature such that the stiffness of the stylet breaks in order to allow the carrier member to curl in order to follow the curvature of the inner walls of cochlea 115.

As one of ordinary skill in the art will appreciate, embodiments of the present invention may be advantageously implemented in a variety of implantable medical device components. In the exemplary application of a cochlear implant, embodiments of the drug delivery system of the present invention are implemented in stimulator unit 134, which is permanently implanted in the recipient. It should be appreciated, however, that embodiments of the present invention may be implemented in temporarily implanted medical device components or in medical device components that are partially implanted. These alternative embodiments and applications of the present invention are described in greater detail below.

Figure 2A:
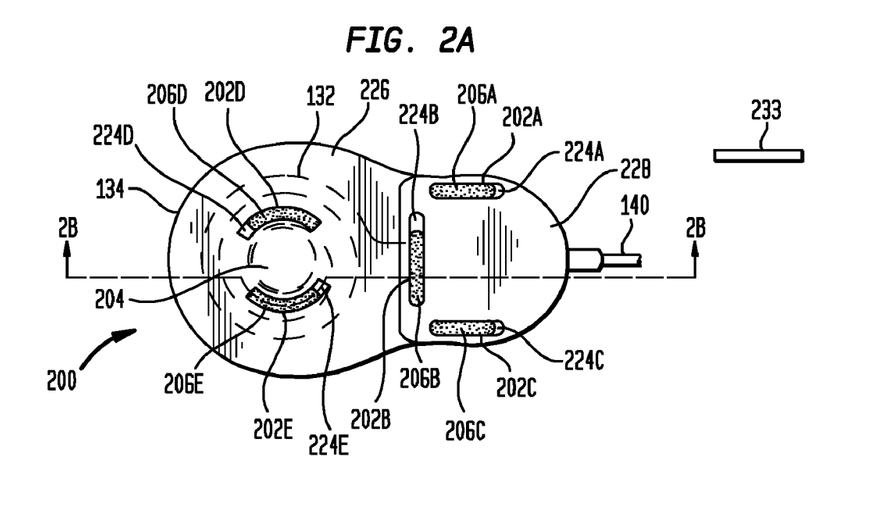
FIG. 2A is a bottom view of an embodiment of the drug delivery system of the present invention implemented in the stimulator unit of the cochlear implant illustrated in FIG. 1.
Figure 2B:
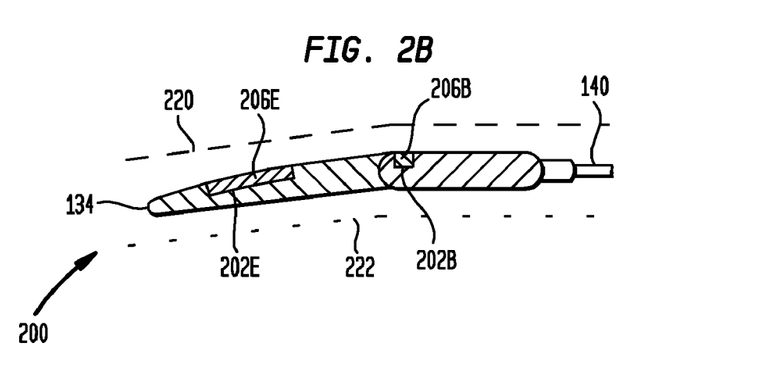
FIG. 2B is a cross-sectional view of the stimulator unit illustrated in FIG. 2A taken along section line 2B-2B, in which the stimulator unit is schematically depicted implanted between a recipient's skin and bone.
Figure 2C:
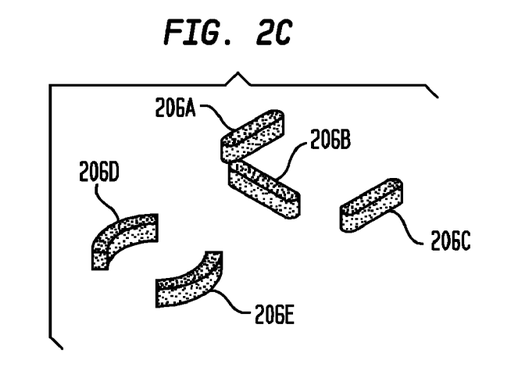
FIG. 2C is a perspective view of the drug delivery modules illustrated in FIGS. 2A and 2B prior to the integration or joining of the drug delivery modules and the stimulator unit illustrated in the same figures, according to an embodiment of the present invention.

FIGS. 2A and 2B are bottom and cross-sectional views, respectively, of one embodiment of the present invention, referred to herein as drug delivery system 200, implemented in an implantable medical device component introduced above, namely, stimulator unit 134 of FIG. 1. In FIG. 2A, stimulator unit 134 is shown in isolation, while in FIG. 2B stimulator unit 134 is shown implanted between a recipient's skin 220 and bone 222 (both shown schematically for ease of illustration). Perspective views of the drug delivery modules shown in FIGS. 2A and 2B are depicted in FIG. 2C.

Drug delivery system 200 comprises, in this embodiment, a housing 228 which forms the bottom surface of stimulator unit 134. Housing 228 has five recesses 202A-202E formed in its exterior surface. In stimulator unit 134, housing 228 is a hermetically-sealed, biocompatible rigid housing configured to be implanted in a recipient's mastoid bone. Rigid housing 228 provides protection for various electronic components mounted inside the housing. It should be appreciated that housing 228 may be a single casing as shown, or may be some portion of the component housing, such as half of a clam shell housing.

Stimulator unit 134 further comprises a solid silicone housing 226 having a coil 132 embedded therein. As noted, internal coil 132 inductively receives power and coded signals transmitted by external assembly 122 (FIG. 1). Internal coil 132 forwards the power and data to electronics contained within rigid housing 228 of stimulator unit 134 which applies the coded signal to cochlea 115 (FIG. 1) via implanted electrode assembly 140 (FIG. 1).

Upon or subsequent to the implantation of stimulator unit 134 into the recipient, soft silicone housing 226 may be forced to flex slightly while rigid housing 228 does not flex in response to the same pressure. A magnet 204 is disposed within a recess in the top surface of silicone housing 226, and when the medical device is implanted in a recipient, operates with a magnet in external component 122 to maintain the proper relative position of internal coil 132 and external coil 130 (FIG. 1). Thus, in contrast to housing 228 which is rigid and has a cavity in which components are mounted, housing 226 is a volume of silicone in which internal coil 132 is embedded.

Recesses 202A-202C are formed in the bottom surface of rigid housing 228, and are disposed around the outside perimeter of the bottom surface of the housing so as to avoid compromising the hermetic seal of the housing. In contrast, recesses 202D and 202E are disposed in silicone housing 226, around magnet 204, and between turns of internal coil 132, as depicted in FIG. 2C. Thus, as used herein, the terms "implantable component housing," "housing," "cover," and the like, refer to any element of an implantable medical device component that provides an exterior surface for at least a part of the implantable device, and in which a recess may be formed to receive and retain a drug-delivery module.

Drug delivery system also comprises five drug delivery modules 206A-206E each configured to be inserted into a correspondingly-configured recess 202A-202E. It is to be understood that drug delivery modules and recesses may be configured in a wide range of sizes and shapes depending on the particular application. For example, drug delivery modules 206D and 206E are curved so as to fit inside correspondingly-configured (that is, curved) recesses 202D and 202E positioned in the bottom exterior surface of silicone housing 226. In this example, recesses 202D and 202E have substantially the same radius of curvature as the perimeter of magnet 204 and the windings of internal coil 132. Recesses 202D and 202E are circumferentially located around magnet 204. As such, recesses 202D and 202E are not aligned with the recess for magnet 204 thereby insuring the structural integrity of this portion of silicone housing 226.

Also, drug delivery modules 206A-206C have sidewalls that are substantially orthogonal to their respective base and top surfaces, so as to have a rectangular cross-section and correspond to similarly shaped recesses 202A-202C. However, it is to be understood that drug delivery modules 206 may have other cross-sectional shapes such as circular, trapezoidal, rectangular, etc., as well as non-geometric dimensions or any other shape which is suitable for inserting into and securing in correspondingly-configured recesses 202.

Embodiments of the drug delivery system of the present invention may advantageously be used to reduce inflammation following the implantation surgery or prevent bacterial infection. Embodiments of the present invention may also be useful in preventing various biological deposits from developing in the areas surrounding the stimulator unit 134. Multiple drug delivery modules 206 may be distributed around various surfaces of stimulator unit 134 in order to provide a substantial distribution of the drugs disposed on drug delivery modules 206. For example, in FIG. 2A, five drug delivery modules 206A-206E are depicted with openings for recesses 202A-202E along the bottom surface of stimulator unit 134. As shown, three drug delivery modules 202A-202C are disposed within rigid housing 228 and two drug delivery modules 202D-202E are disposed within silicone housing 226.

As shown in FIG. 2A, recess 202 may be designed such that recess 202 has a dimension that is slightly larger than the corresponding dimension of drug delivery module 206 and which does not interfere with the ability of recess 202 to securely retain module 206. For example, in the embodiment illustrated in FIG. 2A, recesses 202 are slightly longer than modules 206. As such, there is a space or gap 224 in each of recesses 202 after insertion of modules 206. Gap 224 in each of recesses 202 provides access to a tool to remove active or spent drug delivery module 206 prior to, concurrently with, or subsequent to the implantable device being implanted in the recipient. A generic or specialized tool may be used to remove an active or spent drug delivery module 206 by inserting a tool 233 into gap 224 and prying or otherwise removing the module from recess 202. Gap 224 may be filled with a soft material such as silicone or other resilient material or plug which may be removed or depressed with a tool in order to access and remove drug delivery module 206. Alternatively, a tool may be designed that pierces the drug-deliver module to withdraw the module from the recess. In such embodiments the recess need not have a dimension that is larger than the analogous dimension of the module; that is, in such embodiments there need not be a space or gap in the recess adjacent to the installed module.

In FIGS. 2A and 2B, drug delivery modules 206 are secured inside corresponding recesses 202 by means of a compression or friction fit. In the compression fit, certain dimensions of drug delivery modules 206 are sized slightly larger than the corresponding dimensions of recesses 202. When drug delivery modules 206 are inserted into recesses 202, drug delivery modules 206 compress slightly in response to the insertion force. Such drug delivery modules 206 will be securely retained in place through compression forces exerted by recesses 202 on modules 206. In addition to compression fits described above, it is to be understood that other techniques may also be used to secure drug delivery modules 206 in corresponding recesses 202. For example, an interference fit may be used for such a purpose in which dimensions of recesses 202 may prevent one or more paths of travel by drug delivery modules 206. In such an embodiment, recesses 206 may have openings through which drugs from drug delivery modules 206 may escape but which are too narrow for, and therefore interfering with, drug delivery modules 206 themselves to be removed.

In addition to compression fits and other interference fits described above, various features such as adhesives, latches, clips, tabs and other mechanisms may be used to secure drug delivery modules 206 inside recesses 202. Bonding may be used to bond drug delivery modules 206 inside recesses 202, as will be described further below. Clips may be formed integrally with drug delivery modules 206 and attached to mating clips disposed inside corresponding recesses 202, as will be described further below. Tabs may be formed along the openings of recesses 202 and configured such that drug delivery modules may be inserted and removed into recesses 202 from the side of stimulator unit 134 underneath the tabs, but prevent drug delivery modules from being removed through those openings of recesses 202. It is to be understood that other methods for securing drug delivery modules 206 inside corresponding recesses 202, now known or later developed, may be used according to the present invention.

According to certain embodiments of the present invention, drug delivery modules may be formed as soft or rigid modules. Additionally, corresponding recesses may also be formed as rigid, soft, or soft-coated recesses. For example, in the embodiment shown in FIGS. 2A-2C, recesses 202D and 202E are disposed in the soft silicone housing and receive and secure, through a compression fit, correspondingly-configured drug delivery modules 206D and 206E which may be manufactured to be soft or flexible. Using soft drug delivery modules 206 in soft recesses 202 ensures that the mechanical properties of the medical device are maintained. Furthermore, soft recesses 202D and 202E may provide a seal around drug delivery modules 206D and 206E such that bacteria and other undesirable substances do not develop or are deposited in crevices between drug delivery module 206 and recess 202. Meanwhile, recesses 202A-202C may be formed as rigid recesses, or as rigid recesses which have a soft coating. Where recesses 202A-202C are formed as rigid recesses, drug delivery modules 206A-206C which are formed as quasi-solid modules may be compression fit therein. Where recesses 202A-202C are formed as rigid recesses having a soft or flexible coating, drug delivery modules 206A-206C which are formed as rigid modules may be compression fit therein.

As shown best in FIG. 2B, when a drug-delivery module 206 is inserted into an associated recess 202, the exposed surface(s) of the drug-delivery module is/are substantially contiguous with the exterior surface of the component housing.

It should also be appreciated that the configuration and location of recesses 202 and drug delivery modules 206 may be selected to minimize adverse effects on or interference with the function and operation, and structural integrity, space allocation and/or other characteristics of the implantable component.

Figure 3A:
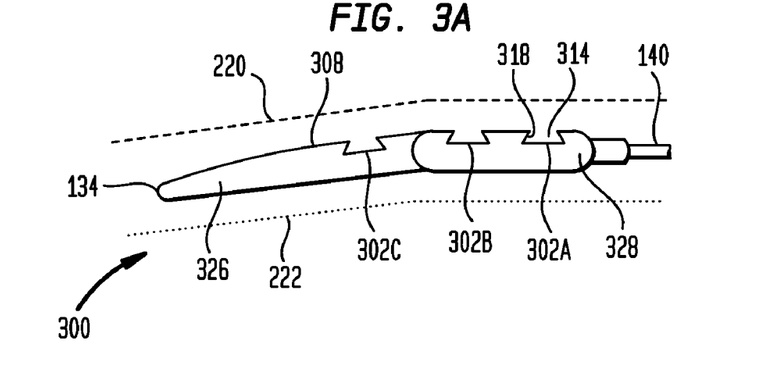
FIG. 3A is a side view of an embodiment of the drug delivery system of the present invention implemented in the cochlear implant stimulator unit illustrated in FIG. 1, in which formed in the bottom exterior surface of the stimulator unit are recesses each of which is configured to receive a drug delivery module, and to securely retain the modules via an interference fit.
Figure 3B:
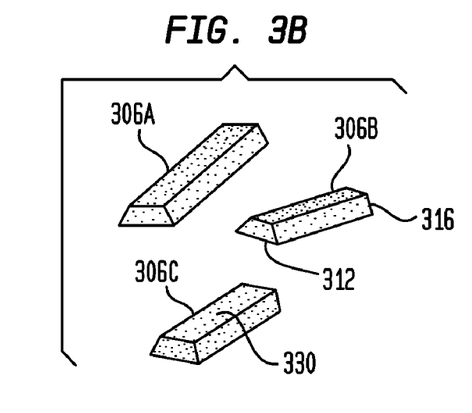
FIG. 3B is a perspective view of drug delivery modules that are correspondingly-dimensioned to be securely retained in the recesses illustrated in FIG. 3A via an interference fit.
Figure 3C:
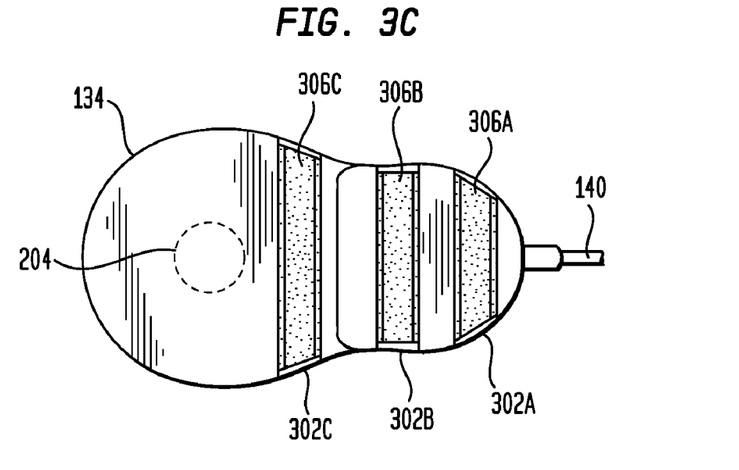
FIG. 3C is a bottom view of the stimulator unit illustrated in FIG. 3A showing the drug delivery modules of FIG. 3B securely retained in the correspondingly-configured recesses in FIG. 3A.

FIGS. 3A, 3B and 3C are side, perspective and bottom views, respectively, of another embodiment of a drug delivery system of the present invention, referred to herein as drug delivery system 300, implemented in stimulator unit 134 (FIG. 1). In FIG. 3A, stimulator unit 134 is shown implanted between a recipient's skin 220 and bone 222, while in FIG. 3C stimulator unit 134 is shown in isolation. A bottom view of the drug delivery modules shown in FIGS. 3A and 3C are depicted in FIG. 3C.

In this exemplary embodiment, drug delivery system 300 comprises three recesses 302A-302C formed in the top exterior surface 308 of stimulator unit 134, and three drug delivery modules 306A-306C configured to be inserted into the correspondingly-configured recesses 302A-302C. In this embodiment of the present invention, stimulator unit 134 comprises a rigid housing 328 and a solid silicone housing 326 as described above with reference to FIGS. 2A-2C. Recesses 302A and 302B are disposed in top surface 308 of rigid housing 328 without compromising the hermetic seal of the housing. Recess 302C is disposed in silicone housing 226.

Recesses 302A-302C are substantially straight to facilitate easy manual insertion of drug delivery modules 306A-306C therein.

As illustrated in FIG. 3B, drug delivery modules 306 have a trapezoidal cross-section so that they may be inserted into correspondingly-shaped trapezoidal recesses 302. Drug delivery modules 306 are inserted from the side of stimulator unit 134. As the base 312 of each trapezoidal drug delivery modules 306 is wider than the opening 314 of recesses 302, an interference fit is provided, as described above. That is, sidewalls 316 of drug delivery modules 306 are interfered by the corresponding sidewalls 318 of recess 302, thus preventing drug delivery modules 306 from being removed through openings of recess 302. Due to this interference fit, drug delivery modules 302 may be removed from stimulator unit 134 only by sliding drug delivery modules 306 sideways along recesses 302.

Drug delivery modules 306 may be manufactured having dimensions such that top surfaces 330 of modules 306 are flush with top surface 308 of stimulator unit 134 when drug delivery modules 306 are inserted. Furthermore, although FIG. 3C shows an exaggerated separation between drug delivery modules 306 and recesses 302, drug delivery modules 306 may be manufactured having dimensions such that there is very little or no gap or crevice created between inserted drug delivery module 306 and corresponding recess 302 upon insertion of drug delivery module 306. Reducing or eliminating gaps or crevices between drug modules and the medical device may be helpful in reducing or avoiding infection, bacterial growth, and undesirable growths and deposits.

It should be appreciated that in alternative embodiments drug delivery modules may be securely retained within correspondingly-configured recesses by something other than the relative dimensions of the recesses and modules. For example, adjacent bone or tissue may be utilized. For example, a component may be implanted in an excavated portion of the recipient's bone such that the surface of the bone obstructs the opening of the recess thereby preventing drug delivery module from existing the recess.

In alternative embodiments of the present invention, top surface 308 of stimulator unit 134 may not have openings on two planes as depicted. Instead, stimulator unit 134 may have openings only on its side which allow drug delivery modules 306 to be inserted into the recess, as well as to allow drugs released by drug delivery modules 306 to escape the recess. As used herein, a recess refers to a receptacle having at least one opening through which an object such as a drug delivery module may be inserted and the same or different opening through which drugs may be released into the patient's body.

It is to be understood that even though recesses 302 are shown as extending across an entire surface of stimulator unit 134, they may also extend only partially across a surface of stimulator unit 134. For example, recess 302B in FIG. 3C may extend only partially across the bottom surface of stimulator unit 134 and receive drug delivery module 306B and create a flush surface on the bottom and side surfaces of stimulator unit 134 at recess 302B. Such a configuration may be beneficial for delivery drugs to specific areas along or near the bottom surface of stimulator unit 134 while allowing design flexibility for the circuitry and other components inside stimulator unit 134.

Figure 4A:
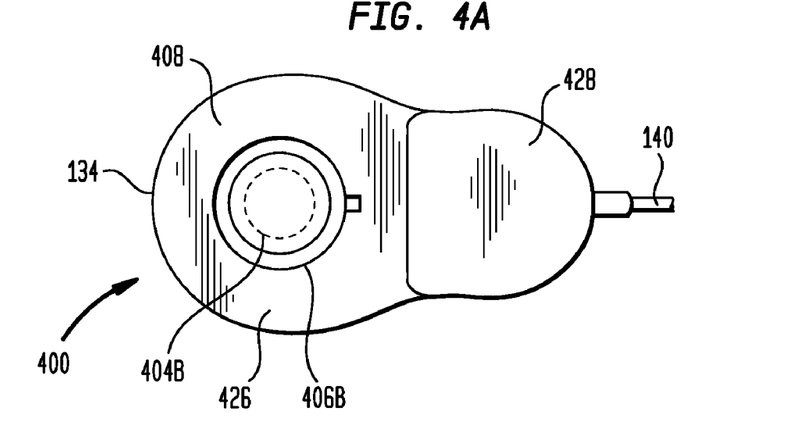
FIG. 4A is a bottom view of an embodiment of the drug delivery system of the present invention implemented in the cochlear implant stimulator unit illustrated in FIG. 1, in which concentric ring-shaped and circular-shaped recesses are formed in the exterior surface of the stimulator unit which securely retain via a friction fit correspondingly-configured drug delivery modules.
Figure 4B:
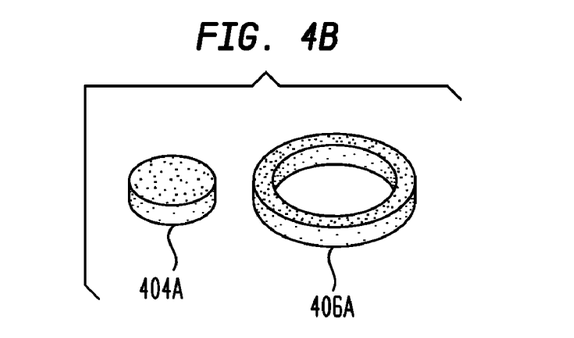
FIG. 4B is a perspective view of drug delivery modules that are correspondingly-configured to be positioned in and securely retained in the recesses illustrated in FIG. 4A via a friction fit.
Figure 4C:
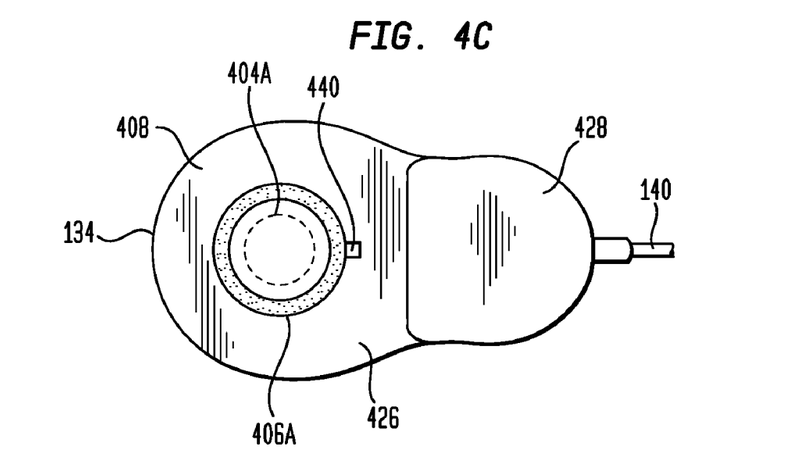
FIG. 4C is a bottom view of the stimulator unit illustrated in FIG. 4A showing the drug delivery modules of FIG. 4B securely retained in the recesses illustrated in FIG. 4A.

FIGS. 4A, 4B and 4C are perspective and bottom views of another embodiment of a drug delivery system of the present invention, referred to herein as drug delivery system 400. In FIG. 4A, stimulator unit 134 is shown in isolation. Perspective views of drug delivery modules 404A and 406A are depicted in FIG. 4B. In FIG. 4C, stimulator unit 134 is shown with drug delivery modules 404A and 406A inserted in recesses 404B and 406B, respectively. Drug delivery system 400 comprises two recesses 404B and 406B formed in the top exterior surface (not shown) and bottom surface 408 of stimulator unit 134, respectively, and two drug delivery modules 404A and 406A having circular and ring shapes, respectively, and configured to be inserted into the correspondingly-shaped recesses 404B and 406B. In this embodiment of the present invention, stimulator unit 134 comprises a rigid electronics housing 428 and solid silicone housing 426 as described above with reference to FIGS. 2A-2C.

Drug delivery modules 406A and 404A are configured to be inserted into correspondingly-configured recesses 406B and 404B, respectively. Modules 406A, 404A are securely retained in recesses 406B, 404B by means of a compression fit between the modules and the recesses. As described above, drug delivery modules 404A, 406A may also be compression fit into coated rigid recesses where the coating is a resilient material which will compress slightly and hold the modules in place upon insertion.

Drug delivery module 404A is a magnet encased in titanium which is itself coated partly or wholly with one or more drugs to form drug delivery module 404A. Providing a drug coating on magnet drug delivery module 404A may be beneficial in providing localized drug delivery near the area of the magnet, to prevent infection or inflammation following implantation surgery or for more long-term treatment of the recipient.

As depicted in FIG. 4C, a space or gap 440 adjacent to recess 406B may be provided to give access for a tool to remove active or spent drug delivery module 406A prior to, concurrently with, or subsequent to the implantable device being implanted in the recipient. A generic or specialized tool may be used to remove active or spent drug delivery module 406A by inserting the tool into gap 440 and prying or otherwise removing the module from recess 406B. Gap 440 may my filled with a soft material such as silicone or other resilient material or plug which may be removed or depressed with a tool in order to access and remove drug delivery module 406A.

Figure 5A:
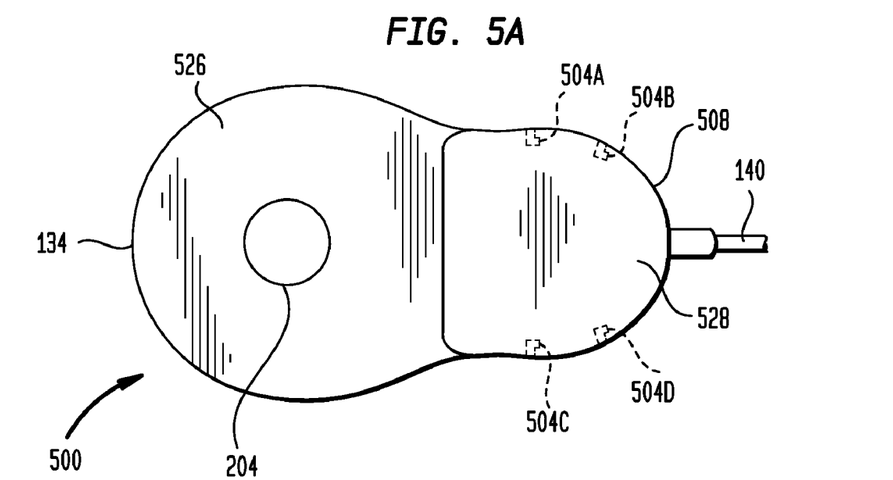
FIG. 5A is a top view of an embodiment of the drug delivery system of the present invention implemented in the cochlear implant stimulator unit illustrated in FIG. 1, in which recesses are formed in the exterior side walls of the stimulator unit to receive and securely retain correspondingly-configured fixation mechanisms extending from drug deliver modules.
Figure 5B:
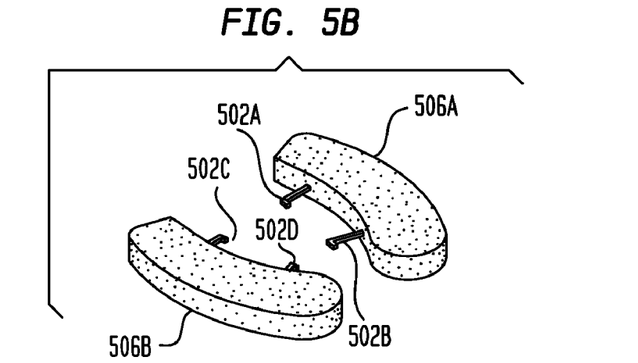
FIG. 5B is a perspective view of drug delivery modules having fixation brackets which are configured to be positioned and securely retained in the recesses illustrated in FIG. 5A.
Figure 5C:
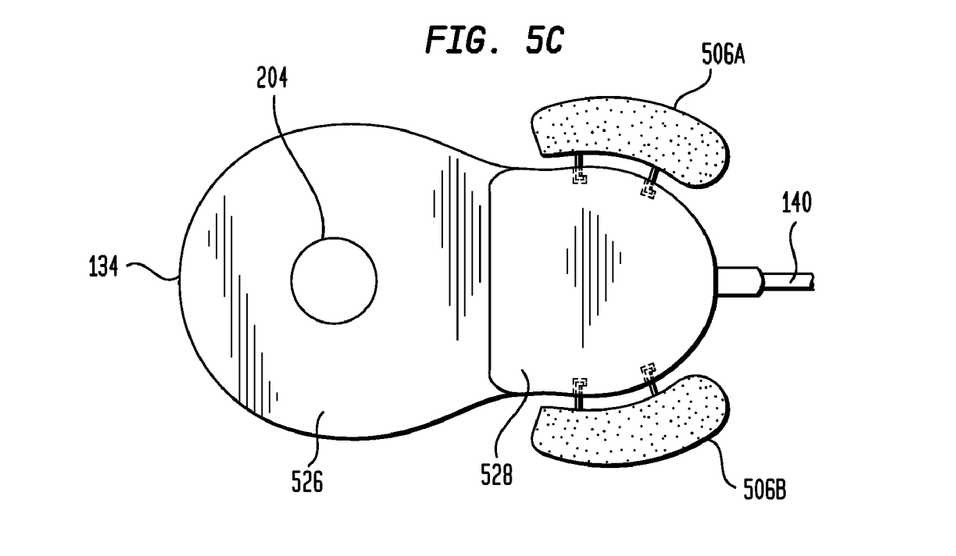
FIG. 5C is a top view of the stimulator unit illustrated in FIG. 5A with the drug delivery modules of FIG. 5B securely retained in the correspondingly-configured recesses formed in the exterior side walls of the stimulator unit.

FIGS. 5A, 5B and 5C are perspective and top views of another embodiment of a drug delivery system of the present invention, referred to herein as drug delivery system 500. FIG. 5A is a top view of drug delivery system 500, in which recesses 504A-504D are formed in the exterior side walls 508 of rigid housing 528 for stimulator unit 134 to receive and securely retain correspondingly-configured fixation mechanisms 502A-502D, respectively, extending from drug delivery modules 506A, 506B. Silicone housing 526 is depicted having magnet 204 embedded therein. FIG. 5B is a perspective view of drug delivery modules 506A, 506B having fixation brackets 502A-502D which are configured to be positioned and securely retained in recesses 504A-504D. FIG. 5C is a top view of stimulator unit 134 illustrated in FIG. 5A with drug delivery modules 506 securely retained in the correspondingly-configured recesses 504. Fixation brackets 502 of drug delivery modules 506 may also carry drugs.

In FIGS. 5B and 5C, brackets 502 are shown as hooks or clips which connect to corresponding connectors disposed in stimulator unit 134, but may also have other shapes and operation. For example, brackets 502 may be shaped as a tab, screw, bracket, or other shapes. Furthermore, drug delivery modules 506 may be attached to stimulator unit 134 or any other part in the implanted component or recipient, including the recipient's bone or skin, by means of adhesives, sutures, screws, among others, to provide a temporary or permanent placement of drug delivery modules 506 near stimulator unit

134. Where drug delivery modules 506 are attached to the recipient's bone or skin, the attached drug delivery modules 506 provides a corral for stimulator unit 134 to prevent lateral movement of the stimulator unit 134 during or following implantation.

It should also be appreciated that the recesses for receiving corresponding drug delivery modules of the present invention may be arranged anywhere on the housing for the implantable medical device. In many applications, the recesses and corresponding drug delivery modules will be configured such that the drug delivery modules are in direct contact with the implantable medical device upon insertion into the recesses. In other embodiments, such as in the embodiment depicted in FIG. 5C, the drug delivery module will be in indirect contact with the implantable medical device through brackets 502 when brackets 502 are inserted into recesses 504 in housing 528. Also, it is to be understood that embodiments of the present invention are not to be limited as to the side of the implantable medical device on which the drug delivery module and corresponding recess may be positioned. As such, the drug delivery modules and corresponding recesses may be positioned on the implantable medical device depending on factors such as intended therapeutic benefits of the drugs, ease of implantation, long-term effects, and others.

It should also be appreciated that the drug loaded modules described above may be formed by one or more layers or sub-parts. In other words, each drug loaded module may be a composite of multiple layers or sub-parts. Each such layer or sub-part may serve a different function, for example, being configured to carry a different drug, releasing the same or different drug at the same or different rate, or having different concentrations of a drug across one or more portions of the drug loaded module.

Furthermore, it is to be understood that drugs may be disposed on just a portion of a drug delivery module depending on the particular application. For example, it may be beneficial for a drug delivery module to have a drug disposed on only a portion of the module, with the remaining portion of the module configured merely as a carrier or supporting member for the medicated portion of the drug delivery module. In one embodiment, the drug delivery module may be a drug-loaded ceramic.

According to a further embodiment of the present invention, the drug delivery module may be constructed of a polymeric material, in which molecules or other components of a drug are disposed within the chemical structure of the drug delivery module. One example of a polymeric material which may be used to construct an embodiment of a drug delivery module of the present invention is silicone. Drugs may be disposed within the silicone drug delivery module such that the drug is released from the drug delivery module.

According to another embodiment of the present invention, the surface of the drug delivery module may be constructed to have microsurface geometry. Such a microsurface geometry may be constructed using nano-technologies, or may be constructed using other technologies presently known or developed in the future. Having a microsurface geometry may enable the drug delivery module to be useful in partially or completely inhibiting growth of bacteria and other biological organisms adjacent to the drug delivery module.

It may be desirable for embodiments of the drug delivery module of the present invention to be constructed of a resorbable material, so that while drugs are being absorbed at the implant site, or after they are absorbed, the drug delivery module may be partially or completely resorbed by the tissue surrounding the implant site. In certain embodiments, the drug delivery module is comprised of a resorbable material that partially or completely degrades over time through interaction with various body fluids. In other embodiments, the drug delivery module is comprised of a resorbable material that partially or completely degrades over time through exposure to body temperatures.

However, it may also be desirable for the drug delivery module to be constructed of a non-resorbable material. The use of a non-resorbable material may offer different benefits from the use of a resorbable material, such as the continued provision of a flush and gapless surface on one or more sides of the implantable medical device or tissue. For example, the drug delivery module may be made of a polymeric material configured to enable drugs to be embedded within the structure of the polymeric material, and to release the drugs either naturally or through the interaction of body fluids or body heat which may permeate the module. Furthermore, the drug delivery module may have micro-surface geometry, such as those possible through advances in nano-technologies, which may limit or inhibit bacteria growth.

As alluded to above, in another embodiment, the drug delivery module may be configured to be bonded into the corresponding recess of the implantable medical device thereby eliminating the need for a non-bonded fitting means (e.g., compression fit, interference fit) between the drug delivery module and the recess of the medical device. In one embodiment, such bonding is performed in a sterile field immediately prior to surgery. Alternatively, such bonding is performed after the medical device is implanted in the patient. In another embodiment, such bonding is performed during manufacturing, such as one of the last few steps of manufacturing.

In one embodiment, the above bonding is performed by disposing a glue layer on the recess so that the drug delivery module may be pressed in prior to surgery. This may be performed manually or with a simple press-tool that aligns the two components and presses them together with a predefined amount of pressure. Alternatively, a liquid glue may be applied between the recess surface and the drug delivery module. In one preferred embodiment, the liquid glue sets and/or cures rapidly. In another embodiment, a UV-cured glue is pre-applied to the component, or applied as a liquid, or is a separate component that is inserted between the drug delivery module and the recess within the implantable medical device. In one embodiment, a liquid perfluoropol polymer such as that described in International Application WO 2007/021620 A2 may be utilized. International Application WO 2007/021620 A2 is hereby incorporated by reference herein. Other adhesives include, but are not limited to, fibrin glues, cyanoacrylates, polyurethane adhesives, silicone adhesives, and UC-cured acrylics. In another embodiment, chemical surface modification may be utilized to attain a desired bonding. For example, in one embodiment, covalently bonded proteins, or sulfonation may be performed to increase the wettability of the surface.

While various embodiments of the present invention have been described above, it should be understood that they have been presented by way of example only, and not limitation. It will be apparent to persons skilled in the relevant art that various changes in form and detail may be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A drug delivery system for an implantable medical device comprising:
   a housing of an implantable component of the medical device having an exterior surface with one or more recesses formed therein; and
   a drug-delivery module that retains at least a quasi-solid state and releasably carries at least one drug,
   wherein the module and housing are physically distinct, and the module and recess are correspondingly dimensioned such that a dimension of the module is sized slightly larger than a corresponding dimension of the recess, thereby securing the module within the recess.

2. The drug delivery system of claim 1, wherein the dimension of the module and the dimension of the recess form an interference fit which comprises physical interlocking of the drug-delivery module in the recess.

3. The drug delivery system of claim 1, wherein the dimension of the module and the dimension of the recess form an interference fit which comprises the drug-delivery module having a friction fit in the recess.

4. The drug delivery system of claim 1, wherein the medical device is a cochlear implant and further wherein the implantable component is a stimulator/receiver device of the cochlear implant.

5. The drug delivery system of claim 1, wherein the drug delivery modules and recesses may be configured in a wide range of sizes and shapes depending on the particular application.

6. The drug delivery system of claim 1, further comprising a tool to remove a drug delivery module from the recess.

7. The drug delivery system of claim 1, wherein the module and recess are configured such that, when a drug-delivery module is inserted into an associated recess, the exposed surface(s) of the drug-delivery module is/are substantially contiguous with the exterior surface of the component housing.

8. The drug delivery system of claim 1, wherein the drug-delivery module is a cartridge.

9. The drug delivery system of claim 1, wherein the drug-delivery module is a tablet.

10. The drug delivery system of claim 1, wherein the drug deliver system has a single drug delivery module per recess.

11. A drug delivery system for an implantable medical device comprising:
    a housing of an implantable component of the medical device having an exterior surface with one or more recesses formed therein; and
    a drug-delivery module that retains at least a quasi-solid state and releasably carries at least one drug,
    wherein the module and housing are physically distinct, and the module and recess are correspondingly dimensioned such that an opening of the recess is more narrow than a corresponding dimension of the module.

12. The drug delivery system of claim 11, wherein wherein when the drug-delivery module is retained in the recess, a surface of the drug-delivery module and a portion of the exterior surface of the housing surrounding the recess form a contiguous component housing surface.

13. The drug delivery system of claim 11, wherein the corresponding dimension is a width of the module.

14. A drug delivery system for an implantable medical device comprising:
    a housing of an implantable component of the medical device having an exterior surface with one or more recesses formed therein; and
    a drug-delivery module that retains at least a quasi-solid state and releasably carries at least one drug,
    wherein the module and housing are physically distinct, and the module and recess are correspondingly dimensioned such that the module may be securely retained within the recess, and
    wherein the housing is a hermetically-sealed, biocompatible rigid housing having mounted therein operational components of the medical device.

15. A drug delivery system for an implantable medical device comprising:
    a housing of an implantable component of the medical device having an exterior surface with one or more recesses formed therein; and
    a drug-delivery module that retains at least a quasi-solid state and releasably carries at least one drug,
    wherein the module and housing are physically distinct, and the module and recess are correspondingly dimensioned such that the module may be securely retained within the recess,
    wherein the recess has a dimension that is slightly larger than the corresponding dimension of the drug delivery module thereby forming a gap in the recess after insertion of the drug-delivery module, the gap providing access to a removal tool to facilitate removal of the module from the recess, and
    wherein the drug delivery system has an a single drug delivery module per recess.

16. A method for implanting a drug delivery system in connection with an implantable medical device, comprising:
    obtaining a drug-delivery module that releasably carries at least one drug;
    producing, independently of the drug-delivery module, a housing for the implantable medical device component, the housing having an exterior surface with at least one recess formed therein, wherein the module(s) and recess (es) are correspondingly configured such that a dimension of the module is sized slightly larger than a corresponding dimension of the recess; and
    inserting the drug-delivery module into the recess subsequent to the device's manufacture such that the module is secured in the recess as a result of the dimension of the module being sized slightly larger that the corresponding dimension of the recess.

17. The method of claim 16, wherein the action of inserting the module into the recess includes moving the module from outside the recess and outside the housing into the recess.

18. The method of claim 17, wherein the action of inserting the module into the recess includes snapping the module into the recess.

19. The method of claim 17, wherein the action of inserting the module into the recess includes inserting the module into the recess such that a surface of the drug-delivery module and a portion of the exterior surface of the housing surrounding the recess form a contiguous component housing surface.

20. The method of claim 17, wherein the medical device is a cochlear implant and further wherein the implantable component is a stimulator/receiver device of the cochlear implant.

21. The method of claim 17, wherein the housing is a hermetically-sealed, biocompatible rigid housing having mounted therein operational components of the medical device.

22. The method of claim 17, wherein the action of inserting the module into the recess includes inserting only one module into one recess such that upon completion of the method, the drug delivery system has a single drug delivery module per recess.

23. The method of claim 17, further comprising the action of removing the drug delivery module from the recess utilizing a tool.

24. A method for implanting a drug delivery system in connection with an implantable medical device, comprising:
   obtaining a drug-delivery module that releasably carries at least one drug;
   obtaining a housing for the implantable medical device component, the housing having an exterior surface with at least one recess formed therein, wherein the module(s) and recess(es) are correspondingly configured such that a dimension of the module is sized slightly larger than a corresponding dimension of the recess,; and
   inserting the drug-delivery module into the recess subsequent to the device's manufacture such that the module is secured in the recess as a result of the dimension of the module being sized slightly larger that the corresponding dimension of the recess.

* * * * *